US00PP17863P3

(12) United States Plant Patent

Roose et al.

(10) Patent No.: US PP17,863 P3

(45) Date of Patent: Jul. 10, 2007

(54) MANDARIN TREE NAMED 'TANGO'

(50) Latin Name: *Citrus reticulata*
Varietal Denomination: Tango

(75) Inventors: Mikeal L. Roose, Riverside, CA (US); Timothy E. Williams, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/220,875

(22) Filed: Sep. 6, 2005

(65) Prior Publication Data

US 2007/0056064 P1 Mar. 8, 2007

(51) Int. Cl.
*A01H 5/00* (2006.01)

(52) U.S. Cl. ..... Plt./201

(58) Field of Classification Search ..... Plt./201, Plt./202

See application file for complete search history.

(56) References Cited

U.S. PATENT DOCUMENTS

PP8,378 P * 9/1993 Vardi et al. ..... Plt./201
PP10,480 P 7/1998 Nadori
PP13,460 P2 * 1/2003 Vardi et al. ..... Plt./202

OTHER PUBLICATIONS

Froneman et al, Promising seedless citrus selections from the ITSC mutation breeding programme, ITSC Information Bulletin, vol. 17, No. 12, 1996, pp. 12–16.*

Topics in Subtropics Newsletter, vol. 2, No. 1, Jan.–Mar. 2004 found on the Internet on Aug. 24, 2006 at <http://ceventura.ucdavis/newsletterfiles/Topics_in_Subtropics4818.pdf>.*

* cited by examiner

*Primary Examiner*—Kent Bell
*Assistant Examiner*—June Hwu
(74) *Attorney, Agent, or Firm*—Townsend and Townsend and Crew LLP

(57) ABSTRACT

A new mandarin variety called 'Tango' is distinguished by production of fruit that combines mid to late season maturity, moderately large fruit size, very smooth rind texture with a deep orange color, and a rich, sweet flavor. It further distinguishes itself by being very low seeded and easy to peel.

8 Drawing Sheets

Latin name of the genus and species: The mandarin cultivar of this invention is botanically identified as *Citrus reticulata.*

Variety denomination: The variety denomination is 'Tango'.

BACKGROUND OF THE INVENTION

'Tango' is a mandarin selection developed at Riverside, Calif. from an irradiated bud of the diploid mandarin cultivar 'W. Murcott', a mid-late season maturing variety. The pedigree of 'W. Murcott' mandarin is unknown but is believed to be a seedling selection from a 'Murcott' Tangor tree produced in an open-pollinated field. The cultivar 'W. Murcott' from which 'Tango' was derived may be identical to a mandarin cultivar known as 'Afourer' and also as 'Nadorcott'. The name 'W. Murcott' was assigned to a mandarin cultivar which was imported into the United States as buds in 1985 from Morocco. 'Afourer' and 'Nadorcott' are known to have originated in Morocco. 'Nadorcott' was patented in the United States in 1997 under U.S. Plant Pat. No. 10,480 (filed in January 1997).

'Tango' originated as a single plant and was asexually reproduced by grafting of budwood onto rootstocks. 'Tango' was selected and propagated as follows. Irradiation of budwood from registered "W. Murcott" trees in Lindcove, Calif. was accomplished in June, 1995 at Riverside using 50 Gray units of gamma irradiation from a Cobalt-60 irradiation source. Buds from this irradiation were propagated onto various rootstocks in the greenhouse at Riverside where they were grown to field-plantable-sized trees. These trees were planted in June 1996 at Riverside. Fruit production and evaluation began in 1998. One tree from this irradiated population (propagated on 'C32' citrange rootstock) distinguished itself from the others in having fruit that had very low seed counts with excellent fruit quality and normal fruit production characteristics in comparison to the original 'W. Murcott' cultivar. After two seasons of fruiting, this tree (now named 'Tango'), was selected for further trials in 1999 and in January 2000 buds were taken and propagated onto 'Carrizo' and C35 citrange rootstock. Budwood was also sent in April 2000 for evaluation of disease status and elimination of viruses and other pathogens as needed.

Twenty trees were planted at Riverside in June 2001. Fruit production on these 20 trees commenced in 2003. In October 2001 two trees of 'Tango', which had been produced from budwood that had been tested and certified as tristeza-free, were sent to Lindcove, Calif. where they were planted in the *citrus* breeding block. Further propagations from the original selection tree in 2001 were made at Riverside and in June 2002 twenty trees were planted at Irvine, Calif., and 15 trees were planted at Santa Paula, Calif.

Fruit production of these propagated trees (at Lindcove, Irvine and Santa Paula) commenced in 2003 (a few trees at each site) and 2004 (all trees at all sites). In July 2002 budwood was taken from the Lindcove trees and topworked onto a navel orange/'Carrizo' citrange tree at Lindcove. In September 2002 eighteen trees, produced from budwood from trees at Lindocove were planted at Arvin, Calif. In August 2003 thirty-six additional trees were propagated at Lindcove from budwood taken from the Lindcove trees and in April 2004, twelve were planted in at Thermal, Calif., and in June 2004, twenty-four trees (twelve at each site) were planted at two sites, Lindcove and Woodlake, Calif. All trials were propagated on 'Carrizo' and 'C35' citrange rootstocks.

BRIEF SUMMARY OF THE INVENTION

The present invention provides a novel mandarin variety having the characteristics described and illustrated herein. The variety, 'Tango', is a mandarin selection developed at the University of California Riverside from an irradiated bud of the diploid mandarin cultivar 'W. Murcott', a mid-late season maturing variety. 'Tango' combines mid to late season maturity, moderately large fruit size, very smooth rind texture with a deep orange color, and a rich, sweet flavor. It further distinguishes itself by being very low seeded (<1 seed/fruit) and very easy to peel.

Mid to late season maturing mandarin cultivars in production include 'W. Murcott' mandarin (the original cultivar from which 'Tango' was derived), 'Murcott' Tangor, 'Fortune' mandarin, 'Ortanique' mandarin, 'Temple' Tangor, late-maturing Clementina selections including 'Hernandina' and 'Nour', 'Dancy' mandarin and 'Minneola' tangelo. All of these cultivars will be seedy if grown in the presence of a pollenizer. Some, including the Clementina selections, 'Fortune', 'Ortanique', and 'Page' mandarins will have few seeds if no pollenizer is present. Recently released mid to late season cultivars that are very low-seeded include 'Gold Nugget' (unpatented), 'TDE2' mandarin hybrid (Shasta Gold®) having U.S. Plant Registration No. PP15,461, 'TDE3' mandarin hybrid (Tahoe Gold®) having U.S. Plant Registration No. PP15,703, and 'TDE4' mandarin hybrid (Yosemite Gold®), having U.S. Publication No. 2003/0237120. 'Tango' differs from these cultivars in having fruit with a smoother rind texture that are easier to peel. Trees of 'Tango' show less alternate bearing than these cultivars. Additional differences (summarized in Table 6) distinguish it from each of these cultivars.

DETAILED DESCRIPTION OF THE INVENTION

Figure 1:
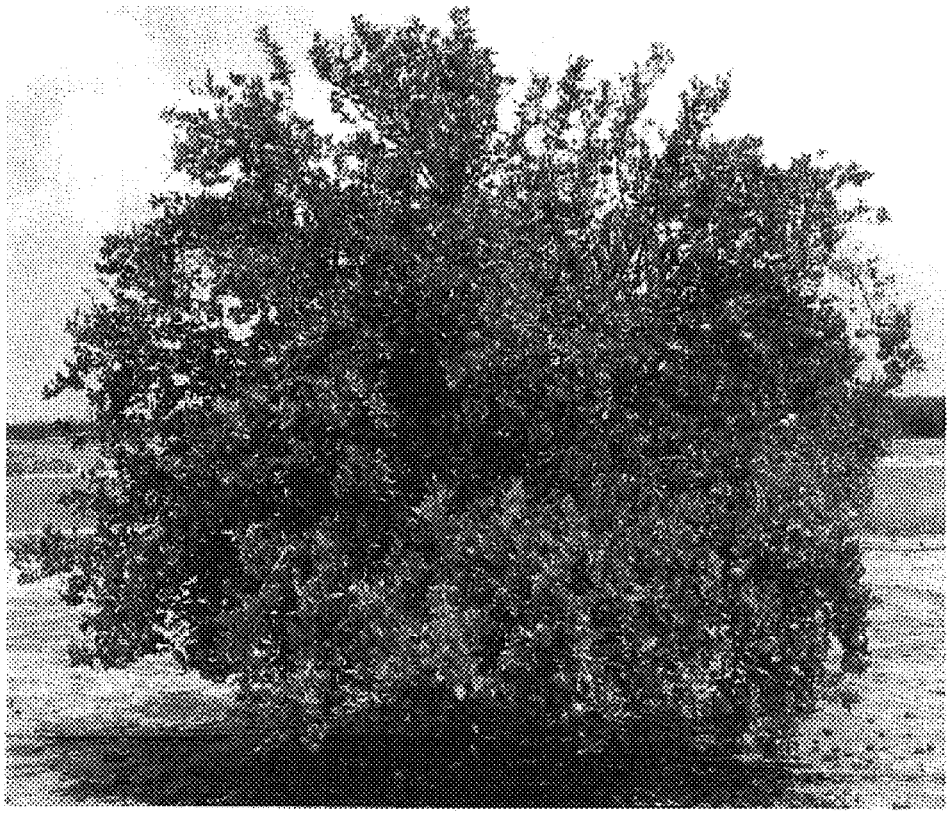
FIG. 1 illustrates an eight-year-old tree of 'Tango' on 'C32' citrange rootstock.
Figure 2:
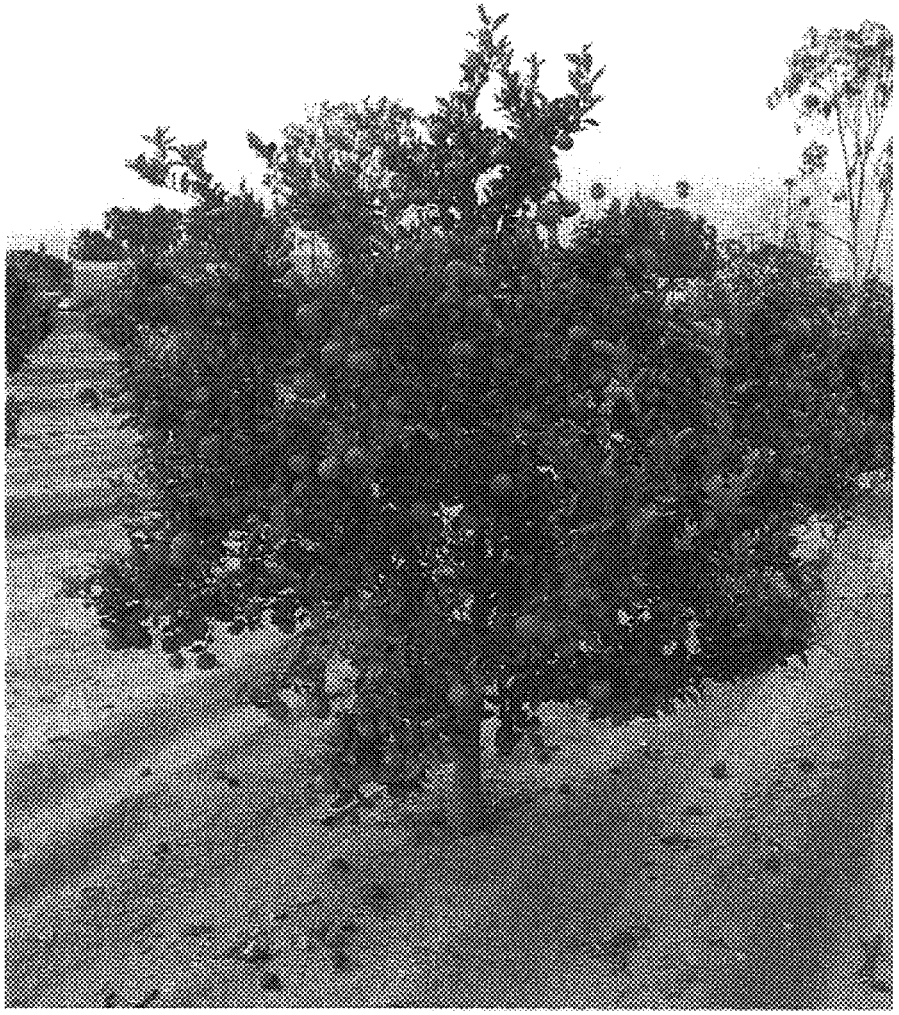
FIG. 2 illustrates a three-year-old tree of 'Tango' on 'Carrizo' citrange rootstock.
Figure 3:
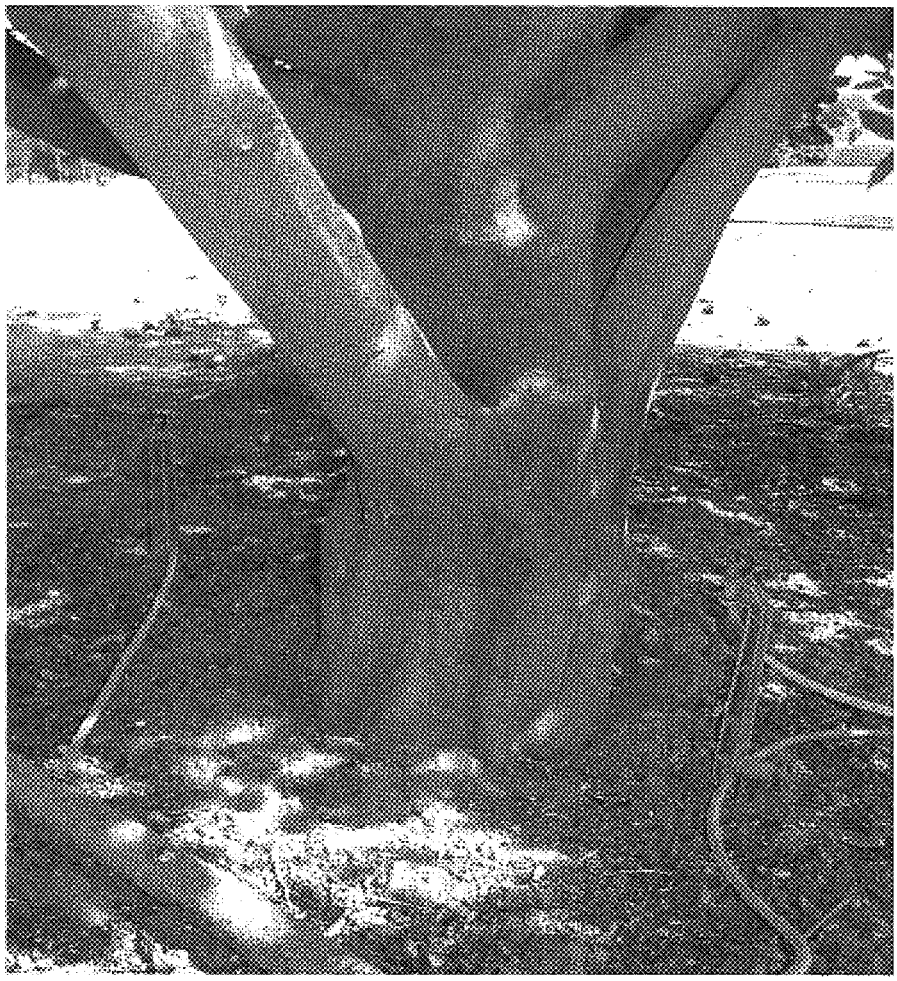
FIG. 3 illustrates the bud-union and scaffold branching of 'Tango' on 'C32' citrange rootstock.
Figure 4:
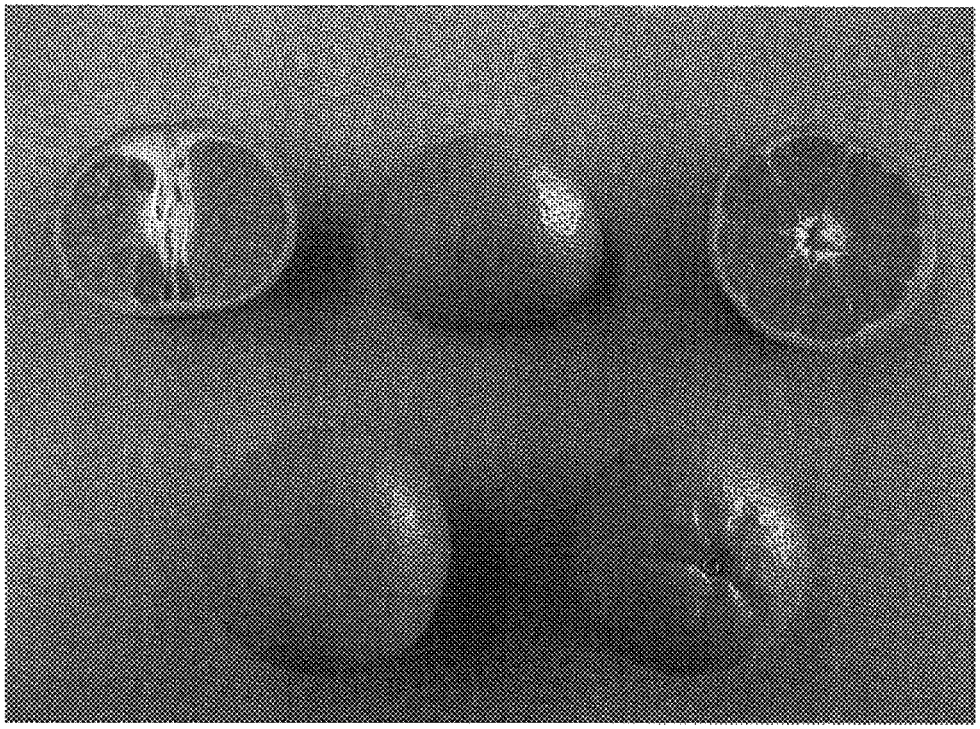
FIG. 4 illustrates fruit of 'Tango' sampled from a three-year-old tree on 'Carrizo' citrange rootstock at Riverside in February, 2005.
Figure 5:
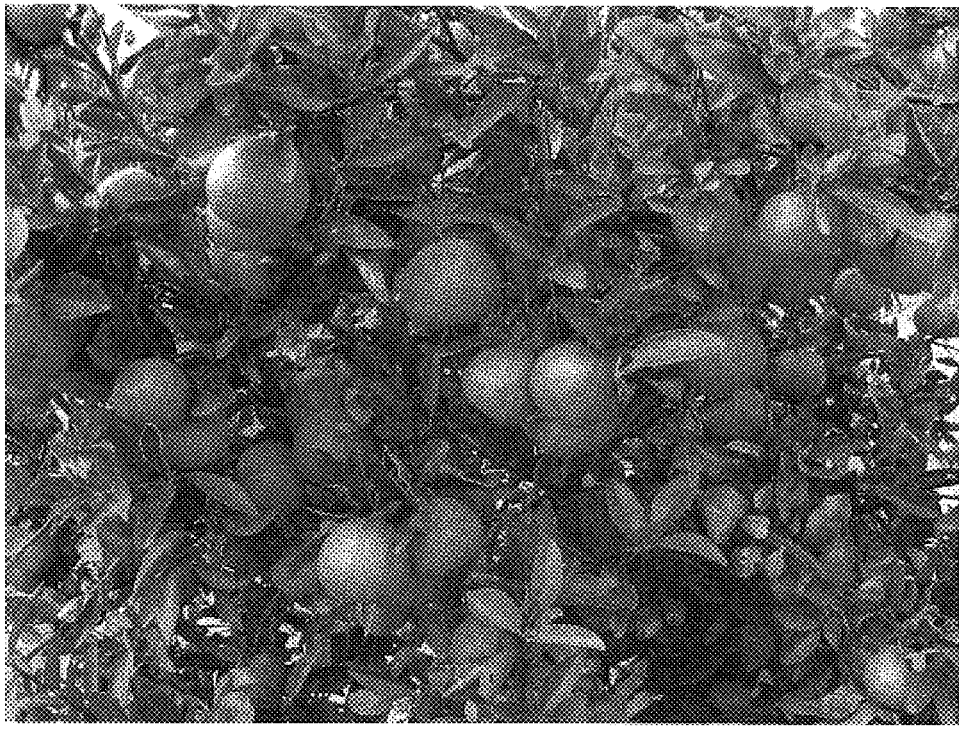
FIG. 5 illustrates fruit clusters of 'Tango' on a three-year-old tree on 'Carrizo' citrange rootstock at Riverside in February, 2005.
Figure 6:
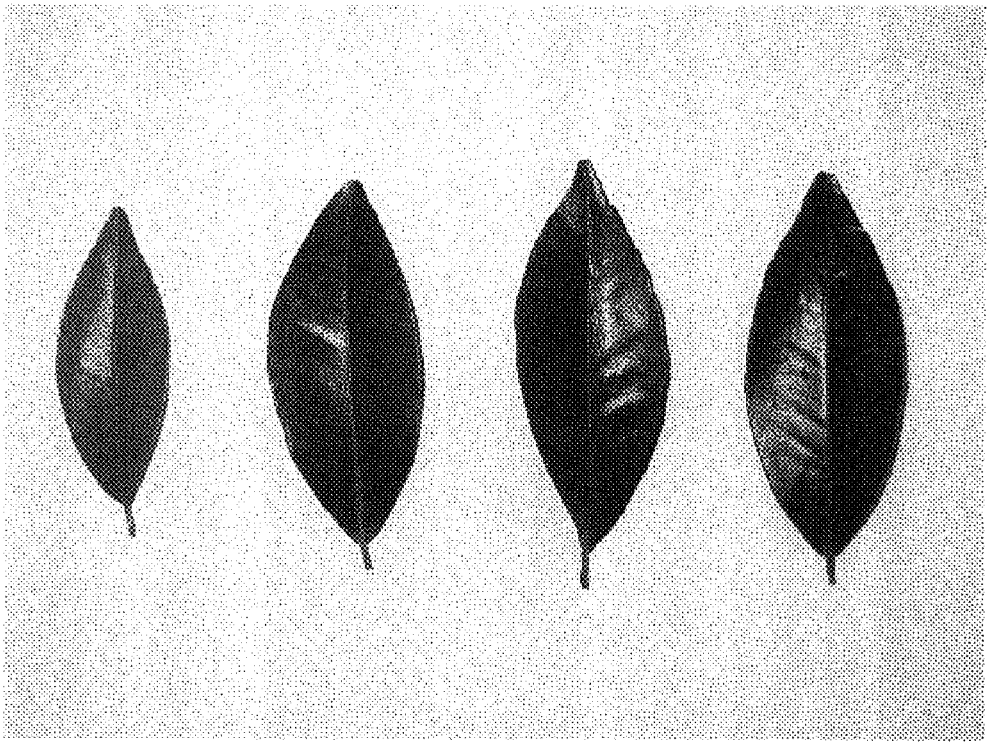
FIG. 6 illustrates various stages of leaves of 'Tango'.
Figure 7:
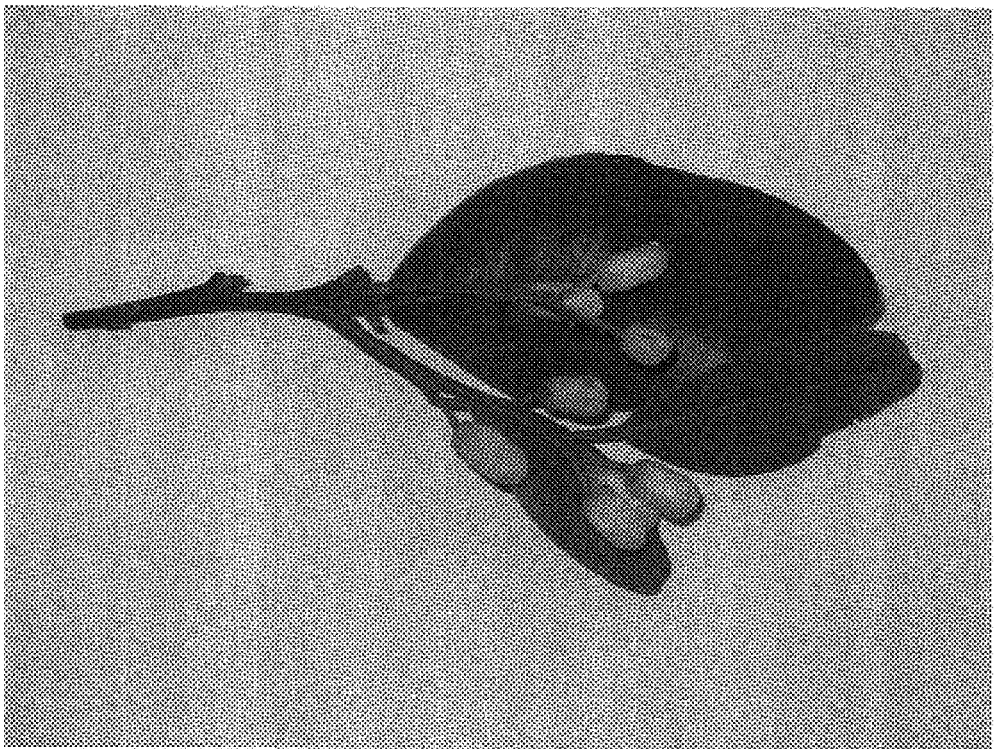
FIG. 7 illustrates floral inflorescence of 'Tango' with closed flowers.
Figure 8:
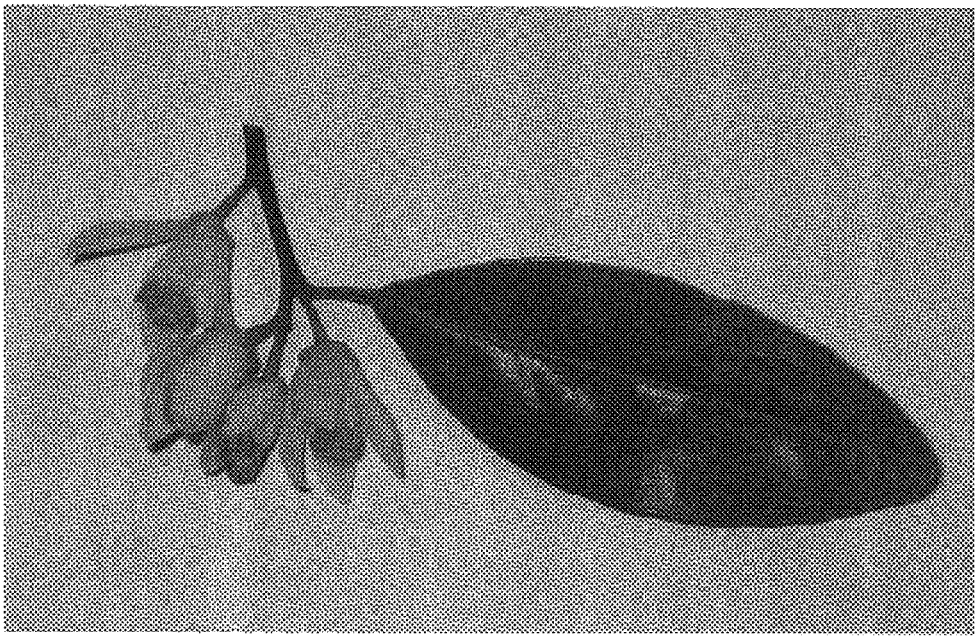
FIG. 8 illustrates floral inflorescence of 'Tango' with open flowers.

Evaluation of 'Tango' began on the original tree at Riverside in 1998 and has continued annually until the present. Tree size, growth and fruit production characteristics and fruit quality characteristics have been compared in these evaluations to 'W. Murcott' mandarin from the same field block. Three and four-year-old 'Tango' trees in trials at Riverside, SCREC, Lindcove and Santa Paula, which were reproduced from the original 'Tango' selection as described above, have also been evaluated from one to two years of fruiting (see Tables 2, 4 and 5). The properties of 'Tango' were found to be true to type and transmissible by asexual reproduction in comparing these plantings with the original 'Tango' selection.

Tree size and growth characteristics of 'Tango' have been consistent with 'W. Murcott' throughout the evaluation. Growth of both the 'W. Murcott' and the 'Tango' selection has been generally upright in the first four years followed by a tendency to grow into a more spherical shape in ensuing years. The nine-year-old 'Tango' tree at Riverside is 3.7 m high and 3.8 m wide with a normal upright growth habit yielding a canopy volume of 29.0 $m^3$. In comparison nine-year-old 'W. Murcott' control trees have averaged 3.8 m tall and 3.8 m wide yielding a canopy volume of 29.8 $m^3$ while sixteen-year-old 'W. Murcott' trees have averaged 4.2 m tall and 4.7 m wide on 'Carrizo' citrange rootstock (canopy volume=50.4 $m^3$) and 3.9 m high and 4.4 m wide on 'C35' citrange rootstock (canopy volume=41.0 $m^3$). Scion circumference for 'Tango' on C32 rootstock was 55.5 cm with the rootstock circumference 60.8 cm. Scion circumference for the nine-year old 'W. Murcott' trees averaged 56.9 cm on 'Carrizo' rootstock while sixteen-year-old 'W. Murcott' trees averaged 59.7 cm on 'Carrizo' rootstock and 55.2 cm on 'C35' rootstock. In the younger multi-location trials three-year-old 'Tango' trees on 'Carrizo' rootstock have averaged 1.9 m in height and 1.3 m in diameter with canopy volumes of 1.75 $m^3$ and trees on 'C35' rootstock averaged 2.0 m in height and 1.4 m in diameter with canopy volumes of 2.05 $m^3$.

'Tango' distinguishes itself by being very low seeded (<1 seed/fruit) in all situations of cross-pollination, differing from 'W. Murcott' which will set up to 10–20 seeds/fruit in cross-pollinated situations. In Riverside, Calif., 'Tango' fruit matures in winter (late January). 'Tango' holds its fruit quality characteristics through April. Fruit size is moderately large (59 mm) averaging 90 grams per fruit. Fruit are deeply oblate in shape with a deep orange rind color and a very smooth rind texture. Flesh color is deep orange and finely textured, fruit are juicy, with a rich, sweet flavor when mature, and are easy to peel. Tree growth habit is upright with excellent production commencing in the second year after planting. Alternate bearing does not appear to be a significant problem. 'Tango' was known throughout experimental evaluation as 'W. Murcott' IR1 (for 'W. Murcott' IRradiated selection #1). The Royal Horticultural Society (R.H.S) color numbering system is used herein for the color description of the rind, seed, bark, leaf, flower, flesh color and other interest of the 'Tango' mandarin hybrid tree.

Leaves of 'Tango' are ovate in shape and concave in cross section, with an acute apex with weak emargination and a convex base and are dark-green in color. Petioles are short and normal lacking wings. The selection lacks thorns. Flowers of 'Tango' are hermaphroditic with greenish-white petals and orangish-yellow anthers and are borne in clusters. In Riverside, Calif. buds form in late-February. Flowering occurs in late-March and continues through April. The flowers have a medium fragrance. Pollen viability for 'Tango' is very low (<5% germination), pollen grains are smaller (18–20 microns) and pollen production is sparse (10–15%) in comparisons to 'W. Murcott' (78% pollen germination, pollen grains 32–34 microns in diameter).

Fruit of 'Tango' are deeply oblate in shape with no neck. The fruit has a slightly concave basal end (moderately depressed) with a truncate (slightly depressed) distal end and a non-persistent style. The fruit is medium sized for a mandarin (classed as Large by State of California standards) averaging 59 mm in diameter and 48 mm in height with a very smooth, deep orange rind color (RHS Orange N25A) and relatively inconspicuous, slightly depressed oil glands. The rind is slightly adherent at maturity (easy to peel) and relatively thin averaging 3.0 mm in thickness. The fruit interior has a fine flesh texture with 9–10 segments and a semi-hollow axis of medium size at maturity. The fruit are juicy averaging slightly over 50% juice and average 90.6 g in weight. Fruit from trees on 'Carrizo' and 'C35' citrange rootstocks average 11.1–13.1% soluble solids and 0.97–1.19% acid in January at four trial locations in California increasing to 13.5–14.4% soluble solids and 0.54–0.82% acid in April. The fruit average less than 0.5 seeds per fruit in the presence of cross-pollination at all locations. Seeds, when present, are polyembryonic, slightly greyed-yellow in color (RHS 162D) with greyed-yellow (RHS 163D) colyledons and a greyed-orange (RHS 164B) inner seed coat. When present, the seeds are 9 mm long and 5 mm wide and are oval with a slightly pointed, flattened seed coat on the radical end of the seed.

TABLE 1

Tree, leaf, flower and seed characteristics (for nine-year-old tree) of 'Tango' mandarin. Data from Riverside, Calif.

| | |
|---|---|
| Tree height | 3.7 m |
| Crown diameter | 3.8 m |
| Crown shape | Upright when young changing to spherical as tree matures |
| Trunk circumference (for scion) (on C32 rootstock) | 55.5 cm measured 25 cm above the soil line, 8 cm above the bud union |
| Trunk circumference (for rootstock) (on C32 rootstock) | 66.0 cm measured 10 cm above the soil line, 7 cm below the bud union |
| Trunk surface texture | smooth |
| Bud-union characteristics (citranges) | Slightly benched |
| Trunk surface texture | smooth |
| Bud-union characteristics (citranges) | Slightly benched |
| Rootstock-scion compatibility | Excellent (with citranges) |
| Tree vigor | Vigorous |
| Bark color | RHS Grey-Brown N199A |
| Leaf shape | Ovate |
| Leaf cross-section | Concave |
| Leaf blade length | 63.9 mm |
| Leaf blade width | 28.9 mm |
| Leaf apex | Acute with weak emargination |
| Leaf Base | Convex |
| Leaf abaxial color | RHS Yellow-Green 146B |
| Leaf adaxial color | RHS Green 137A |
| Petiole length | 5.9 mm |
| Petiole width | 1.5 mm |
| Petiole color | RHS Green 137A |
| Thorniness | Not present |
| Inflorescence type | Clustered |
| Flowering habit | Flowers once per year |
| Flower size | 11.0 mm (medium) |
| Flower structure | Complete |
| Petal color | RHS Green-White 157C |
| Anther color | RHS Yellow-Orange 15C |
| Pollen size | 18–20 microns |
| Pollen viability | Very low (<5%) |

TABLE 2

Fruit characteristics of 'Tango' mandarins from four trial sites (Riverside, SCREC, Lindcove and Santa Paula)

| | |
|---|---|
| Fruit shape | Deeply oblate |
| Fruit diameter | 59.0 mm ± 7.5 |
| Fruit height | 48 mm ± 3.2 |
| Fruit: shape of basal end | Slightly concave (moderately depressed) |
| Fruit: shape of distal end | Truncate (slightly depressed) |
| Fruit neck | Not present |
| Style | Not persistent |
| Rind texture | Smooth |
| Oil glands | Conspicuous, slightly depressed |
| Rind Color | RHS Orange N25A |
| Rind thickness | 3.0 mm |
| Albedo thickness | 1.5 mm |
| Albedo color | RHS Orange 24D |
| Rind adherence | Moderately weak |
| Rind separation | Slight |
| Flesh (pulp) color | RHS Orange-Red N30D |
| Flesh (pulp) texture | Fine |
| Number of segments | 9–10 |
| Axis: structure | Semi-hollow |
| Axis: size | Medium |
| Navel presence | Not present |
| # Seeds/fruit | 0.22 (cross pollinated conditions) |
| Seed embryony | Polyembryonic |
| Seed coat color | Greyed-Yellow 162D |
| Seed cotyledon color | Greyed-Yellow 163D |
| Seed inner coat color | Greyed-Orange 164B |
| Fruit weight | 90.4 g |
| % Juice | 50.2% |
| % Soluble solids (at maturity) | 12.5% |
| % Acid (at maturity) | 0.98% |
| Season of maturity | Mid-late (late January-February) |
| Fruit holding ability on tree past maturity | 2–3 months |
| Fruit quality after storage (5.6° C., 31 days) | Excellent |

'Tango' is a mid to late season maturing diploid mandarin that combines medium large sized fruit of excellent quality and production with very low seed content even in mixed plantings. It would likely be successful in the mid- to late-season marketing window that currently has very few low seeded cultivars.

'Tango' mandarin can be grown according to accepted cultural practices for most mandarin varieties including planting densities of 150–250 trees per acre, normal fertilization and pest control practices, and the use of standard rootstocks for mandarins. Pruning may enhance production and health of the tree if applied after the second year of full fruit production. Other rootstocks adapted to more marginal growing conditions of salinity, high pH or very heavy soils may be useful in those conditions.

Fruit production of 'Tango' begins in the second year after planting similar to 'W. Murcott'. This is one year ahead of most mandarin cultivars which begin fruiting in the third year after planting. Fruit production on two-year-old trees averaged 10–26 kg, and in three-year-old trees averaged 33–58 kg at the three fruiting trial sites. The original tree at Riverside was similar in fruit production in the second and third years and in years 5, 6 and 7 yielded 98, 90 and 101 kg of fruit respectively indicating that in the earlier years of production the variety does not alternate bear, similar to 'W. Murcott'.

TABLE 3

Crop yields for 'Tango' and 'W. Murcott' (control trees) at three trial sites over two years, 2003/2004 and 2004/2005.

| Site | Selection | # Trees | Tree Age (yrs) | Rootstock |
|---|---|---|---|---|
| Riverside | 'Tango' | 12 | 3.5 | Carrizo |
| Riverside | 'Tango' | 8 | 3.5 | C35 |
| Riverside | 'Tango' (mother) | 1 | 9 | C32 |
| Riverside | 'W. Murcott' control | 2 | 9 | Carrizo |
| Santa Paula | 'Tango' | 10 | 2.5 | Carrizo |
| Santa Paula | 'Tango' | 5 | 2.5 | C35 |
| Santa Paula | 'W. Murcott' control | 3 | 2.5 | Carrizo |
| Irvine | 'Tango' | 9 | 2.5 | Carrizo |
| Irvine | 'Tango' | 10 | 2.5 | C35 |

| Site | 2003/4 Mean Yield (kg) | 2003/4 Yield Range (kg) | 2004/5 Mean Yield (kg) | 2004/5 Yield Range (kg) |
|---|---|---|---|---|
| Riverside | 12.8 | 9.3–17.9 | 49.8 | 35.1–58.3 |
| Riverside | 12.0 | 7.8–14.9 | 46.9 | 31.4–55.2 |
| Riverside | 101.3 | 101.3 | 42.3 | 42.3 |
| Riverside | 88.5 | 82.4–96.6 | 93.7 | 88.1–99.3 |
| Santa Paula | * | * | 22.2 | 14.3–25.7 |
| Santa Paula | * | * | 22.7 | 15.1–26.4 |
| Santa Paula | * | * | 16.9 | 14.1–18.7 |
| Irvine | * | * | 5.9 | 1.4–18.6 |
| Irvine | * | * | 10.7 | 2.3–17.3 |

*-not fruiting

TABLE 4

Seed counts (average number of seeds per fruit) for 'Tango' and 'W. Murcott' (control trees) at three trial sites over two years, 2003/2004 and 2004/2005.

| Site | Selec-tion | Tree Age (yrs) | Rootstock | 2004/5 Mean Seeds/ Fruit | 2004/5 Seed Count Range |
|---|---|---|---|---|---|
| Riverside | 'Tango' | 3.5 | 'Carrizo' | 0.21 | 0.0–0.80 |
| Riverside | 'Tango' | 3.5 | 'C35' | 0.09 | 0.0–0.28 |
| Riverside | 'Tango' (mother) | 9 | 'C32' | 0.22 | NA |
| Riverside | 'W. Murcott' control | 9 | 'Carrizo' | 12.3 | 10.1–14.4 |
| Santa Paula | 'Tango' | 2.5 | 'Carrizo' | 0.04 | 0.0–0.16 |
| Santa Paula | 'Tango' | 2.5 | 'C35' | 0.06 | 0.0–0.20 |
| Santa Paula | 'W. Murcott' control | 2.5 | 'Carrizo' | 6.8 | 6.2–7.4 |
| Irvine | 'Tango' | 2.5 | 'Carrizo' | 0.04 | 0.0–0.07 |
| Irvine | 'Tango' | 2.5 | 'C35' | 0.07 | 0.0–0.13 |
| Lindcove | 'Tango' | 2.5 | 'Carrizo' | 0.12 | 0.10–0.15 |
| Lindcove | 'W. Murcott' control | 15 | 'Carrizo' | 9.1 | 6.8–13.0 |

TABLE 5

Mean and standard deviation (S.D.) of soluble solids, acid and solids/acid ratio for 'Tango' and 'W. Murcott' (control trees) at three trial sites, 2004/2005 crop year.

| Site | Date | Soluble Solids % Carrizo | S.D. | Soluble Solids % C35 | S.D. | % Acid Carrizo |
|---|---|---|---|---|---|---|
| Riverside | Jan. 6, 2005 | 12.8 | 0.31 | 12.6 | 0.50 | 1.39 |
| Riverside | Feb. 10, 2005 | 13.2 | 0.44 | 13.0 | 0.26 | 1.06 |
| Riverside | Mar. 9, 2005 | 13.7 | 0.13 | 13.8 | 0.33 | 0.89 |
| Riverside | Apr. 18, 2005 | 14.4 | 0.50 | 14.1 | 0.37 | 0.78 |
| Santa Paula | Jan. 24, 2005 | 13.1 | 0.29 | 13.3 | 0.36 | 0.97 |
| Santa Paula | Feb. 15, 2005 | 13.3 | 0.19 | 13.7 | 0.39 | 0.90 |
| Santa Paula | Mar. 15, 2005 | 13.8 | 0.33 | 14.2 | 0.44 | 0.80 |
| Santa Paula | Apr. 20, 2005 | 14.1 | 0.36 | 14.7 | 0.45 | 0.76 |
| Irvine | Jan. 20, 2005 | 12.1 | 0.66 | 11.9 | 0.49 | 1.03 |
| Irvine | Feb. 11, 2005 | 12.9 | 0.38 | 12.8 | 0.55 | 0.89 |
| Irvine | Mar. 14, 2005 | 13.9 | 0.44 | 13.5 | 0.26 | 0.78 |
| Irvine | Apr. 13, 2005 | 13.8 | 0.48 | 13.5 | 0.41 | 0.67 |
| Lindcove | Jan. 18, 2005 | 11.1 | 0.26 | NA | NA | 1.19 |
| Lindcove | Feb. 16, 2005 | 12.3 | 0.16 | NA | NA | 1.00 |
| Lindcove | Mar. 17, 2005 | 13.0 | 0.20 | NA | NA | 0.88 |

| Site | S.D. | % Acid C35 | S.D. | S/A Ratio Carrizo | S/A Ratio C35 |
|---|---|---|---|---|---|
| Riverside | 0.16 | 1.22 | 0.08 | 9.2 | 10.3 |
| Riverside | 0.08 | 1.09 | 0.06 | 12.5 | 11.9 |
| Riverside | 0.09 | 0.93 | 0.03 | 15.4 | 14.78 |
| Riverside | 0.13 | 0.82 | 0.06 | 18.5 | 17.2 |
| Santa Paula | 0.19 | 0.89 | 0.07 | 13.5 | 14.9 |
| Santa Paula | 0.09 | 0.84 | 0.07 | 14.7 | 16.3 |
| Santa Paula | 0.16 | 0.81 | 0.06 | 17.3 | 17.5 |
| Santa Paula | 0.10 | 0.73 | 0.10 | 18.6 | 20.1 |
| Irvine | 0.14 | 1.10 | 0.12 | 11.7 | 10.8 |
| Irvine | 0.13 | 0.90 | 0.14 | 14.5 | 14.2 |
| Irvine | 0.08 | 0.77 | 0.11 | 17.8 | 17.5 |
| Irvine | 0.08 | 0.54 | 0.11 | 20.6 | 25.0 |
| Lindcove | 0.15 | NA | NA | 9.3 | NA |
| Lindcove | 0.11 | NA | NA | 12.3 | NA |
| Lindcove | 0.06 | NA | NA | 14.8 | NA |

NA - not applicable (no trees of this type in trial)

'Tango' mandarin exhibits very low seed numbers (<1 seed per fruit) in all fruit under all conditions of cross-pollination. Additionally, preliminary evaluations indicate that pollen from 'Tango' has very low germination rates in culture (<5%) and does not appear to cause seeds in other mandarins, causing no seed in selected Clementine mandarin cultivars when hand pollinated onto those selections. A comparison of 'Tango' with other low-seeded late-season mandarins is provided in Table 6. 'Tango' is distinctive and superior in having a smoother rind, less alternative bearing, and smaller fruit size that may be preferred in some markets.

TABLE 6

Comparison of 'Tango' with other late season, low-seeded mandarins. Data for Riverside, Calif.

| Trait | 'Tango' | 'TDE2' | 'TDE3' | 'TDE4' | 'Gold Nugget' |
|---|---|---|---|---|---|
| Maturity | late January–February | mid February | January–February | February | late January–February |
| Seeds per fruit | 0.22 | 0.02 | 0.29 | 0.32 | <0.1 |
| RHS rind color | orange N25A | orange-red N30D | orange-red N30C | orange-red N30C | orange 25A |

TABLE 6-continued

Comparison of 'Tango' with other late season, low-seeded mandarins. Data for Riverside, Calif.

| Trait | 'Tango' | 'TDE2' | 'TDE3' | 'TDE4' | 'Gold Nugget' |
|---|---|---|---|---|---|
| Rind texture | very smooth | slightly pitted | papillate | Smooth | bumpy |
| Fruit weight (g) | 90 | 185 | 134 | 175 | 108 |
| Fruit height/width | 0.81 | 0.78 | 0.85 | 0.78 | 0.88 |
| Alternate bearing | Low | medium | medium-high | medium-high | high |

Fruit storage trials included storage of washed but not waxed fruit at 5.6° C. for up to 60 days with fruit samples taken every 14 days for analysis. Data indicate that the storage characteristics of 'Tango' is excellent with no noticeable loss of rind quality or color, no significant indication of fungal disease problems and no significant loss of size or deterioration in juice quality or taste over the 60 day storage period.

No susceptibilities to plant or fruit diseases or to pests beyond those normally associated with *citrus* species have been observed.

What is claimed is:

1. A new and distinct variety of mandarin hybrid tree having the characteristics essentially as described and illustrated herein.

* * * * *